United States Patent [19]

Seifert

[11] Patent Number: 5,378,236
[45] Date of Patent: Jan. 3, 1995

[54] BALLOON DILATATION CATHETER WITH INTEGRAL DETACHABLE GUIDEWIRE

[75] Inventor: C. Vaughn Seifert, Boxborough, Mass.

[73] Assignee: C. R. Bard, Inc., Murray Hill, N.J.

[21] Appl. No.: 883,350

[22] Filed: May 15, 1992

[51] Int. Cl.⁶ .............................................. A61M 29/02
[52] U.S. Cl. ...................................... 604/96; 606/194
[58] Field of Search ............................. 604/95–104, 604/280, 164; 606/192–194

[56] References Cited

U.S. PATENT DOCUMENTS

| | | |
|---|---|---|
| Re. 32,348 | 2/1987 | Pevsner . |
| 4,311,146 | 1/1982 | Wonder . |
| 4,327,734 | 5/1982 | White, Jr. . |
| 4,341,218 | 7/1982 | Ü . |
| 4,346,712 | 8/1982 | Handa et al. . |
| 4,364,392 | 12/1982 | Strother et al. . |
| 4,395,806 | 8/1983 | Wonder et al. . |
| 4,441,495 | 4/1984 | Hicswa . |
| 4,456,011 | 6/1984 | Warnecke . |
| 4,471,779 | 9/1984 | Antoshkiw . |
| 4,520,823 | 6/1985 | LeVeen et al. . |
| 4,702,252 | 10/1987 | Brooks et al. . |
| 4,932,959 | 6/1990 | Horzewski et al. . |
| 5,045,061 | 9/1991 | Seifert . |
| 5,104,376 | 4/1992 | Crittenden ............................. 604/96 |
| 5,135,487 | 8/1992 | Morrill et al. ........................ 604/96 |
| 5,192,295 | 3/1993 | Danforth et al. ................... 606/194 |
| 5,195,989 | 3/1993 | Euteneuer ........................... 604/280 |

*Primary Examiner*—John D. Yasko
*Attorney, Agent, or Firm*—Morgan & Finnegan

[57] ABSTRACT

A fixed wire balloon dilatation catheter usable in angioplasty is provided with a connection between the guidewire and the catheter which can be ruptured so as to detach the catheter shaft and balloon from the guidewire. The guidewire then can be extended by attaching an extension wire to the proximal end of the guidewire. The catheter shaft and balloon then may be withdrawn from the patient while the guidewire position is maintained. A second catheter then may be advanced over the extended guidewire. In accordance with the method of the present invention, the guidewire is not extended when the second catheter is a monorail catheter.

24 Claims, 3 Drawing Sheets

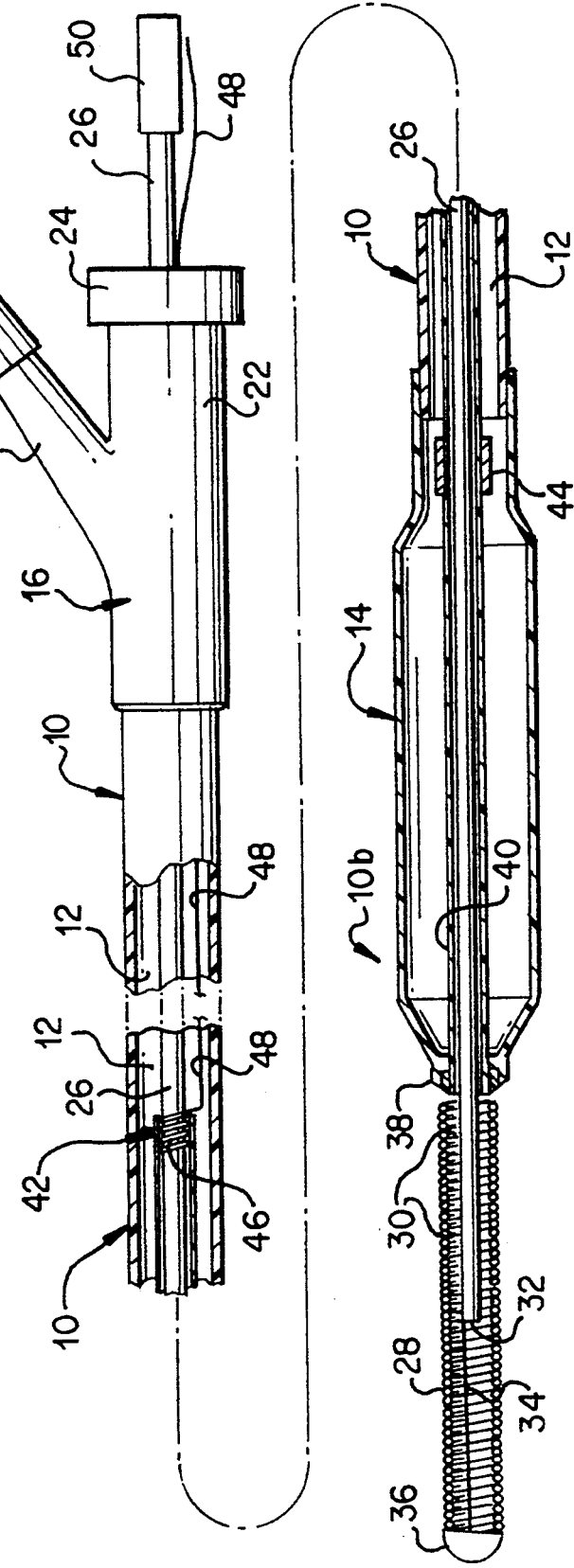
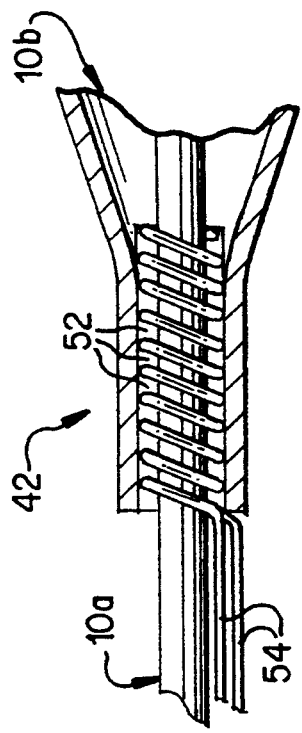
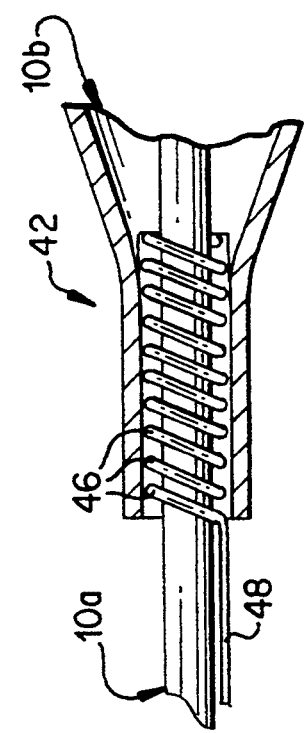

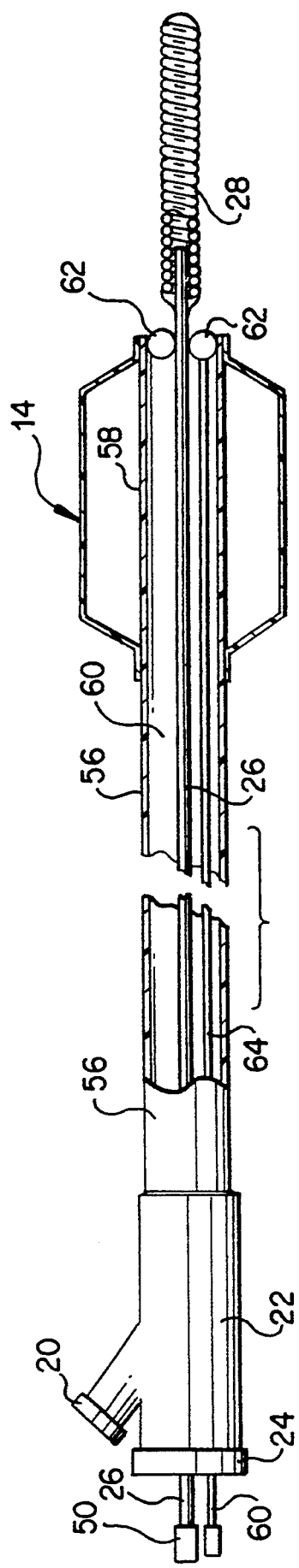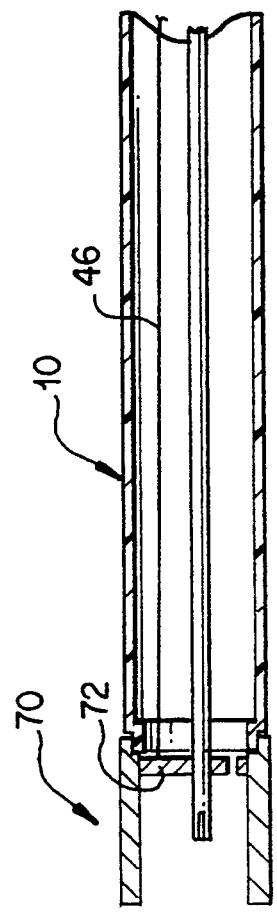

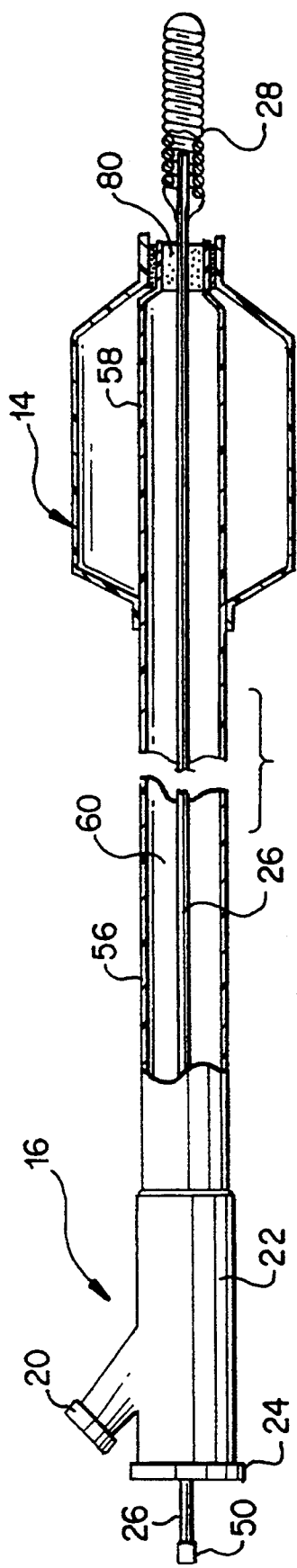
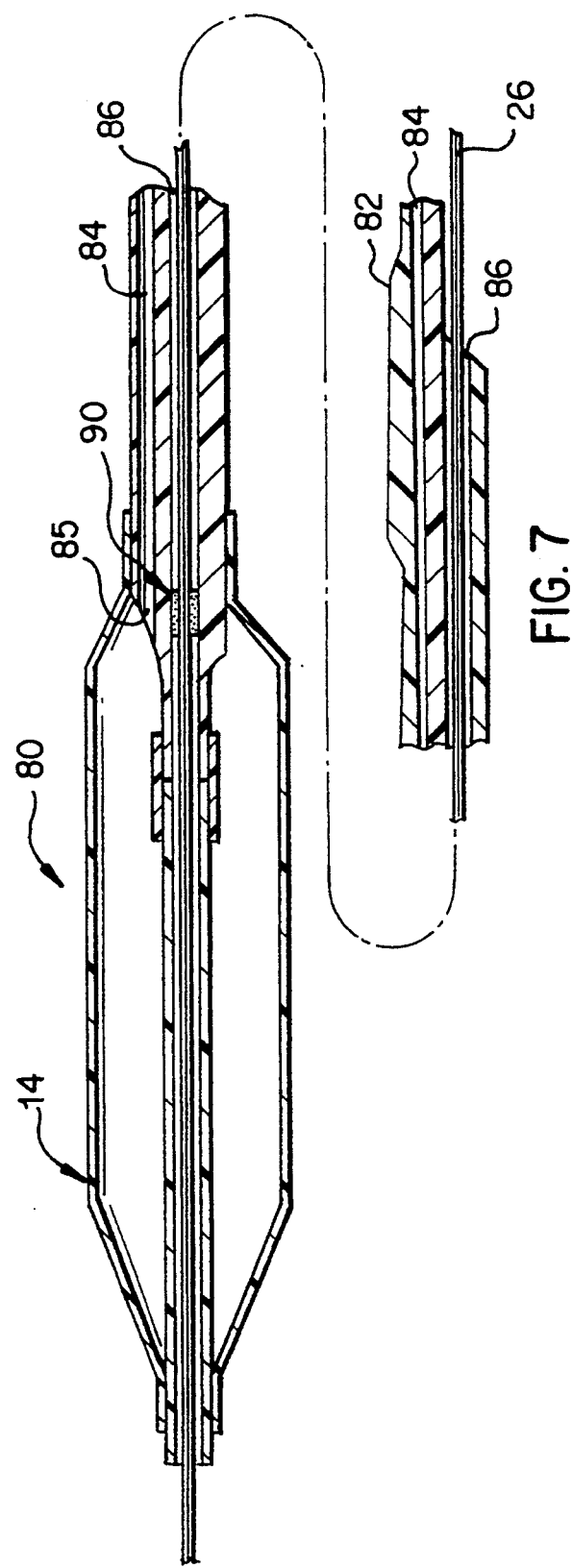

BALLOON DILATATION CATHETER WITH INTEGRAL DETACHABLE GUIDEWIRE

FIELD OF THE INVENTION

This invention relates to balloon dilatation catheter systems used in percutaneous transluminal coronary angioplasty and a method for performing the procedure.

BACKGROUND OF THE INVENTION

This invention relates to improvements in small diameter, low profile dilatation catheters used in angioplasty, particularly coronary angioplasty. The invention concerns a type of angioplasty catheter commonly referred to as a "fixed wire" catheter in which the catheter includes a tubular shaft and an integral guidewire. More specifically, the invention concerns improvements in catheter systems and the manner in which such a catheter can be exchanged for another catheter.

In performing coronary angioplasty, the physician may wish to use a catheter different from the one originally inserted into the patient if the initial selection of catheter balloon size is inappropriate to treat the patient's stenosis or if some other event occurs that would make use of a different catheter desirable. When the catheter is the type that uses a separate movable guidewire, the catheter may be exchanged in a well-known procedure in which an exchange wire is substituted for the movable guidewire (or the length of the guidewire is extended with an extension wire). The catheter then is withdrawn over the exchange wire and the replacement catheter is threaded over the exchange wire and guided to the stenosis.

By maintaining the guidewire in position during the exchange procedure, the replacement catheter is easily and quickly advanced to the stenosis. Such procedure, however, has required the use of an "over-the-wire" catheter system which includes the catheter and a separate movable guidewire received through a guidewire lumen formed in the catheter. With an over-the-wire catheter system, the catheter is easily removed from the patient, leaving the guidewire extended in place so that the next succeeding catheter can be advanced over the guidewire to the site of the stenosis.

The foregoing catheter exchange procedure has not been usable with small diameter, low profile "fixed wire" dilatation catheters. These catheters incorporate an integral guidewire that cannot be separated from the catheter. Thus, when the physician desires to exchange one such dilatation catheter for another, the physician typically withdraws the entire catheter and integral guidewire from the patient's arterial system and then replaces it with the desired catheter.

Withdrawal of the catheter, however, results in loss of position of the catheter in the stenosis. As a result, the new catheter must be remanipulated through the patient's arterial system to position the balloon in the stenosis. This catheter replacement typically involves time-consuming manipulation and steering to guide the catheter and place its balloon within the stenosis. This additional procedure increases the risk of trauma and fluoroscopic radiation to the patient.

U.S. Pat. No. 4,932,959 to Horzewski et al. discloses a catheter having an inflatable collar for securing a portion of the wall forming the inner lumen to the guidewire when inflation fluid under pressure from a second annular passageway fills the inflation chamber. This construction demands a more complex construction and a three-arm adapter having independent sections communicating with individual catheter lumens.

It is therefore desirable to provide an improved system in which catheter exchanges involving small diameter, low profile dilatation catheters of the "fixed wire" type can be effected easily, quickly, with minimal trauma, and without loss of catheter position without complex design changes. It is among the objects of this invention to provide such a system.

It is therefore an object of the present invention to provide at improved angioplasty catheter arrangement having the advantages of a fixed wire catheter but which enables a catheter exchange to be performed without losing position of the guidewire in the patient.

Another object of the present invention is to provide a fixed wire type of angioplasty catheter having an elongate flexible shaft and an integral guidewire, in which the shaft is sealed to the guidewire at a joint that can be ruptured.

A further object of the invention is to provide an angioplasty catheter of the type described in which means are provided for enabling detachment of the shaft and balloon portion of the catheter from the guidewire.

A further object of the invention is to provide an improved method for performing angioplasty with a fixed wire type of catheter.

Additional objects and advantages of the invention will be set forth in the description which follows and, in part, will be obvious from the description and advantages being realized and attained by means of the instrumentation, facts, apparatus, systems, steps and procedures particularly pointed out in the specification.

BRIEF DESCRIPTION OF THE INVENTION

In accordance with the present invention a catheter of the "fixed wire" type is provided in which the catheter shaft carrying the balloon portion of the catheter can be separated from the integral guidewire while the catheter is in the patient. The shaft and balloon portion can be withdrawn, thus leaving the guidewire in the patient. The guidewire then serves to guide succeeding over-the-wire catheters to the stenosis, without loss of guidewire position.

In each of the several embodiments of the invention, the catheter includes an elongate flexible tubular shaft having a balloon at its distal end. The lumen of the tubular shaft defines a passageway by which the balloon can be inflated and deflated. In a first embodiment, the proximal end of the shaft includes a Y-fitting, one branch of which is in communication with the inflation lumen and connectible to an inflation device. An elongate guidewire extends through the inflation lumen and through the other branch of the Y-fitting at the proximal end of the catheter.

In a second embodiment of the invention, the shaft includes a longitudinal end fitting secured to the proximal end of the shaft. The end fitting includes a balloon inflation passage for allowing fluid flow into the shaft.

In this second embodiment or in both embodiments, the distal end of the guidewire shaft extends distally beyond the balloon and terminates in a tapered distal segment. An elongate flexible helical coil is attached to the distally protruding portion of the guidewire shaft. The catheter shaft and its distal region are attached to the guidewire in a manner that effectively seals the inflation lumen and balloon to the guidewire so that the balloon can be inflated and deflated.

In accordance with the present invention, connection means is provided for the "fixed-wire" connection between the catheter shaft and the guidewire and is formed so as to be ruptured and separated from the guidewire. In one embodiment, the proximal end of the guidewire is configured to be attachable to an extension wire, thereby enabling extension of the effective length of the guidewire to a length sufficient to enable a catheter exchange to be performed. Should it be desired to perform a catheter exchange, the physician can extend the length of the guidewire and then detach the catheter shaft from the guidewire. The catheter shaft and balloon then can be withdrawn over the extended guidewire while the position of the guidewire is maintained. After removal of the catheter shaft and balloon, another catheter can be advanced over the extended guidewire while the position of the guidewire is maintained within the body.

The catheter exchange can be simplified if a monorail catheter construction is used as the replacement catheter. Once the bond is ruptured, the first catheter is removed. Because the monorail construction has a shorter guidewire lumen, during replacement and catheter exchange, an extension wire is not needed because the monorail catheter can be slipped over the present guidewire. A modified fitting may be necessary to ensure that the monorail catheter transfer is feasible.

The connection means between the catheter shaft and the guidewire may be formed by an adhesive at the detachment joint. To control separation at the detachment joint, a slender pull wire can be provided by which the integrity of the joint can be disrupted. The distal end of the pull wire may be helically wrapped about the guidewire shaft within the adhesive joint. The proximal end of the pull wire is accessible to the physician at the proximal end of the catheter. By pulling on the pull wire, the joint is ruptured and the catheter and guidewire are separated.

In still another embodiment of the invention, the connection means includes a heatable coil that is incorporated into the detachment joint and conductive wires extend along and within the catheter. The heating element in the joint is activated to effect the separation of the catheter shaft and guidewire.

In yet an alternate embodiment, the connection means includes a catheter that is provided with an inflatable seal which, when inflated, constricts tightly about the guidewire sufficiently to effect a seal between the catheter shaft and the guidewire. A separate inflation lumen is provided for the annular inflatable seal.

In still another embodiment of the present invention, the connection means includes a joint which is formed as an adhesive joint which can be ruptured by ultrasonic energy or back-and-forth movement of the guidewire.

The invention consists of the various parts, constructions, arrangements and improvements shown and described. The accompanying drawings which are incorporated in and constitute a part of the specification illustrate embodiments of the invention and together with the description serve to explain the principles of the invention.

DESCRIPTION OF THE DRAWINGS

The foregoing and other objects and advantages of the present invention will be appreciated more fully from the following description, with reference to the accompanying drawings in which:

FIG. 1 is a fragmented, sectional, somewhat diagrammatic illustration of one embodiment of the catheter;

FIG. 2 is an enlarged sectional view of the connection of the catheter to the guidewire and illustrating one embodiment of the means for rupturing the connection;

FIG. 3 is a view similar to FIG. 2 illustrating a modified embodiment of the means for rupturing the connection between the guidewire and the catheter;

FIG. 4 is a diagrammatic illustration of another embodiment of the invention in which an inflatable member serves as a detachable connection between the catheter and the guidewire;

FIG. 5 is a sectional view of another embodiment of the catheter having a different configuration at the proximal end;

FIG. 6 is another embodiment similar to FIG. 4 and showing a breakable adhesive bond between the catheter and guidewire; and FIG. 7 is a sectional view of another embodiment of the invention in which the seal of the present invention is used in an over-the-wire monorail catheter.

DESCRIPTION OF THE PREFERRED EMBODIMENT

FIG. 1 shows one embodiment of the invention in which the catheter includes an elongate flexible shaft indicated generally by the reference numeral 10. The shaft 10 includes proximal and distal ends 10a and 10b. The shaft is formed from a tube of suitable polymeric material of the type conventionally used in angioplasty catheters such as polyethylene. The overall length of the catheter may be of the order of 150 centimeters. By way of example, the shaft may be of the order of 0.040 inches or less diameter having a wall thickness of the order of 0.005 to 0.010 inches. The tubular shaft defines an internal lumen 12 that communicates with the interior of a balloon 14 at the distal end 10b of the shaft to inflate and deflate the balloon. In the illustrated embodiment of FIG. 1, a Y-fitting 16 is attached to the proximal end 10a of the shaft 10. One leg 18 of the fitting 16 is provided with a luer connector 20 for connection to an inflation and deflation device, such as a syringe. The other leg 22 includes a releasable sealing device 24 such as known in the art as a Tuohy Borst adaptor.

The illustrated catheter is of the "fixed wire" type and includes an integral guidewire 26. The guidewire may be formed from a stainless steel shaft and may have a diameter along most of its length on the order of 0.010 inches to 0.018 inches. The distal portion of the guidewire shaft preferably is tapered to a smaller diameter in order to provide enhanced flexibility at the distal portion of the guidewire. The taper is illustrated only diagrammatically in FIG. 1 and may take a number of forms, such as a continuous taper or a stepped taper, as will be appreciated by those familiar with the art.

A helical coil 28 is secured to the distal tip of the guidewire 26 such as by solder joints 30, with a portion of the helical coil extending distally beyond the distal tip 32 of the main shaft of the guidewire. The distal extension of the coil 28 is highly flexible and presents an atraumatic tip to the interior of the patient's blood vessels. A stainless steel, tungsten or other material shaping ribbon 34 may be extended from the distal soldered joint to a tip soldered joint or a tip weld 36. The tip 36 is rounded to present a smooth surface. In one embodiment, the coil 28 is approximately two centimeters long, has an outer diameter of about 0.014 inches, and may be wound, for example, from 0.003 inch diameter wire, such as 92% platinum, 8% tungsten alloy.

The balloon 14 may be formed from polyethylene terepthalate formed in the manner described in U.S. Pat. No. 4,490,421 to Levy. By way of example, the balloon 14 may be of the order of 1.5 to 2.5 centimeters long and may have a wall thickness of about 0.001 or less. The inflated diameter of the balloon 14 may be between about 1.5 and 4.0 millimeters.

The distal end of the balloon 14 is attached at its distal neck 38 to the distal end of an inner sleeve 40 that extends proximally about the tapered portion of the guidewire shaft. The balloon 14 is adhesively attached at its proximal end to the guidewire shaft 26 at a connection indicated at 42. The inner sleeve 40 is thin-walled and may be formed from a thermoplastic polyamide or other material such as thin-walled polyethylene terephthalate, although the polyamide is preferred. The wall thickness of the inner sleeve 40 preferably is about 0.001 inches or less. The inner sleeve 40 should have an inner diameter slightly greater than the diameter of the guidewire shaft 26 to provide sufficient clearance between the sleeve and guidewire shaft to accept the adhesive and another small wire coil, as will be described. The inner sleeve 40 may, for example, be about 30 centimeters long. Such polyamide sleeves are commercially available in various sizes from PolyMicrotechnology of Phoenix, Ariz.

The inner sleeve preferably has a substantial degree of column strength to resist axial buckling when it is subjected to an axial compressive load, such as when the catheter is advanced through a patient's blood vessel. In addition, the thin wall of the inner sleeve 40 permits a substantial amount of rotation to be absorbed by the inner sleeve; yet the inner sleeve will not buckle under axial loads because of the support provided by the guidewire shaft. It should be understood, however, that even though the inner diameter of the sleeve 40 is close to the outer diameter of the shaft of the guidewire, the frictional characteristics of the two elements are such that the guidewire is free to rotate, particularly, when the device is passed through the curves and tortuous anatomy of the patient's arteries. The polyamide material provides a low coefficient of friction to avoid binding under such circumstances. Similarly, the frictional characteristics between the polyamide inner sleeve 40 and the outer sleeve 10 (which may be polyethylene) is such that they do not restrict proper functioning of the device even when passed through tortuous bends of the arterial anatomy. A radiopaque marker band 44 may be attached to the inner sleeve 40 in the region of the balloon 14 to facilitate fluoroscopic determination of the position of the balloon in the patient's arteries.

From the foregoing, it will be appreciated that the balloon 14 and the shaft 10 and inner sleeve 40 are unattached to the shaft of the guidewire except for the detachable connection at the proximal fitting 22 at the connection 42. The foregoing arrangement provides advantages in reducing the risk of the balloon 14 becoming twisted about the guidewire, as may sometimes occur with other fixed wire catheters. The details of operation of the foregoing arrangement are described in further detail in U.S. patent application Ser. No. 07/269,795 filed Nov. 10, 1988, to which reference is made and which is incorporated herein in its entirety.

In accordance with the invention means is provided for permitting the catheter to be changed while the guidewire remains in place. As illustrated in further detail in FIG. 2, the means includes a connection 42 and a slender wire 46 (on the order of about 0.0003 inches diameter) that is wound in a helical coil about the guidewire shaft within the connection 42. A proximal extension of the wire 48 extends through the lumen 12 of the catheter, alongside the guidewire 26, and through the fitting 24 on the Y-adapter 22 where the pull wire 48 can be grasped and pulled by the physician. The adhesive at the connection 42 is selected with respect to the strength of the pull wire 48 such that when the wire 48 is pulled it will break the adhesive connection between the sleeve 40 and the guidewire shaft sufficiently to separate the two. The adhesive may be, for example, a silicone based adhesive, or a cyanocrylate. Once separated, and with the proximal seal 24 released, the assembly of the shaft 10 and balloon 14 can be withdrawn proximally over the guidewire. Thus, the guidewire can remain in place to provide a path along which a succeeding catheter call be advanced directly to the region of the artery to be treated.

In other embodiments the connector means is used in conjunction with an exchange wire. Thus, in the embodiments illustrated in FIGS. 1-3, 4 and 6, an exchange wire is used to facilitate catheter exchange. As embodied, the proximal end of the guidewire is provided with a connector, indicated diagrammatically at 50, by which an extension wire can be attached to the guidewire 26. The connector may be in the form of a tubular socket or a member insertable into a tubular socket or other arrangement for attachment of the extension wire to the guidewire. Reference is made to U.S. Pat. Nos. 4,917,103; 4,922,923; 4,922,924; 5,031,636; and U.S. patent application Ser. No. 07/206,008 filed Jun. 13, 1988 for a detailed explanation of various systems for attaching a guidewire extension to a guidewire. The disclosures of each of those patents and application are incorporated herein by reference in their entireties.

FIG. 3 illustrates another embodiment of the connector means. In this modified arrangement, the connection 42 for the helical coil 52 is disposed about the guidewire shaft and formed from a resistance heating element in which a pair of electrical conductor wires 54 extend proximally through the proximal fitting 22 where they may be connected to a source of electrical energy. In this embodiment the adhesive at the connection 42 is selected so that it is softened by heat to disrupt the connection 42. Thus, in this embodiment the connection 42 may be ruptured by application of electrical energy. As with the first described embodiment, when the connection is ruptured, the guidewire can be extended in length and the shaft 10, balloon 14, and inner sleeve 40 can be withdrawn without losing guidewire position.

FIG. 4 illustrates an alternate embodiment of the invention in which the connection means between the catheter and the guidewire is effected by an inflatable member carried at the distal end of the catheter which can be tightly constricted about the shaft of the guidewire. This catheter embodiment does not include a sleeve surrounding the guidewire as shown in FIGS. 1-3. The catheter is more configured to an over-the-wire type of catheter. In this embodiment the catheter may include an elongate flexible tubular polymeric shaft 56. The shaft 56 may extend through the balloon 14 to the distal end of the catheter. One or more inflation ports 58 are formed in the shaft to communicate the shaft lumen 60 with the interior of the balloon 14 to inflate and deflate the balloon.

As embodied a connection means is provided to effect a secure seal between the catheter lumen 60 and the guidewire 26 in the form of an annular shaped inflatable element 62 mounted at the distal end of the catheter shaft 15. The annular inflatable element 62 is adapted to receive the shaft of the guidewire 26 and is configured so that when inflated, it is forced into firm constricting contact about the guidewire shaft. The sealing force thus developed should be sufficient to withstand inflation pressures used to inflate the balloon in the intended range of such pressures. A secondary tube 64 is connected to the balloon and inflates and deflates the annular balloon. In the illustrated embodiment, the distal end of the tube is connected to the annular balloon. The proximal end of the tube 64 and the shaft of the guidewire 26 protrudes through the end fitting 22. A suitable fitting 66 is attached to the proximal end of the secondary tube 64 for connection to a suitable inflation and deflation device.

In use the catheter shaft 56 and guidewire 26 are assembled with the guidewire extending through the inflatable balloon element 62. The combined system can be navigated to the patient's arteries to the site of treatment. In that configuration the device may exhibit desirable characteristics such as those of a "fixed wire" catheter. However, it should be understood that in connection with the embodiment illustrated in FIG. 4, the catheter and guidewire may be configured as an over-the-wire system in which the catheter shaft 56 is sufficiently large to permit withdrawal of the guidewire through the catheter lumen. However, when the device is dimensioned and configured to function as a small diameter, low profile "fixed wire" catheter in which the guidewire cannot be removed through the catheter shaft, the annular balloon 58 may be deflated and withdrawn over the guidewire 26, an extension wire having been previously attached to the proximal end of the guidewire. The catheter exchange then can proceed in the usual fashion.

When a monorail catheter construction is used as the replacement catheter, the exchange method is simplified. When the bond is ruptured, the original catheter is removed. Because the monorail construction has a shorter guidewire lumen, during replacement and catheter exchange, an extension wire is not needed-the monorail catheter is slipped onto the present guidewire.

FIG. 5 represents a connecting means or an alternate end fitting in which a luer connector is not used. Instead, a longitudinally extending proximal end fitting, illustrated generally at 70, is removably fitted to the proximal end of the shaft 10. As illustrated, the proximal end fitting 70 includes a transverse wall portion 72 through which the guidewire extends. The pull wire 46, if used, may be connected to the end wall portion 72. An inflation passage 74 is formed within the end wall 72. The end fitting 70 is configured for connection to an inflation device (not shown), in which fluid flows into the end fitting, through the inflation passage 74, and into the catheter and balloon. The end fitting 70 may include a wire clamp for facilitating easy dismantling and removal from the tube.

Referring now to FIG. 6, an alternate embodiment similar to FIG. 4 is illustrated in which the seal at the proximal end of the tube is effected by an adhesive 80 forming a bond which can be ruptured by mechanical movement or ultrasonically induced vibration. Suitable adhesives known to those skilled in the art may be used to provide such a bond which may be broken mechanically by back-and-forth movement or by vibration ultrasonically induced in the adhesive bond.

Thus, it will be appreciated that the invention provides an arrangement by which a catheter having the desirable characteristics of a small diameter, low profile "fixed wire" catheter may be exchanged for another catheter without losing the position of the guidewire element. Additionally, a monorail type over-the-wire catheter may be used. With such a catheter construction, an extension wire is no longer necessary.

FIG. 7 illustrates a catheter 80 of monorail configuration with the connection of the present invention incorporated therein to provide for a monorail configured catheter having fixed wire characteristics. The monorail catheter 80 includes a proximal end portion 82 in which an inflation lumen 84 is offset from a guidewire lumen passage 86. The inflation lumen 84 extends into the proximal end of the balloon where it forms a discharge opening 85 through which the fluid for inflating the balloon is discharged. As illustrated, the guidewire 26 extends through the passage 86 and the balloon, and is fixed to the balloon by means of a breakable seal 90. In the illustrated embodiment, the seal 90 is similar to that illustrated in FIG. 6, in which induced ultrasonic energy or other mechanical movement can rupture the seal, thus permitting the catheter to be removed from the patient. Once the bond is ruptured, the catheter is removed from the patient and a new monorail catheter is substituted. Alternatively, the seal can be formed from an adhesive bond having a pull wire (not shown) for breaking the bond, such as discussed above with reference to the embodiment shown in FIGS. 1-3. The seal 90 also can be located at the distal end of the balloon.

The advantages of the invention are achieved in a manner that reduces the time necessary in order to perform the exchange thereby reducing exposure of the patient to fluoroscopy and, in general, reducing the duration of the overall procedure. It should be understood, however, that the foregoing description of the invention is intended merely to be illustrative thereof and that other embodiments, modifications and equivalents may be apparent to those skilled in the art without departing from its spirit.

Having thus described the invention what I desire to claim and secure by Letters Patent is:

1. A balloon angioplasty catheter comprising:
   an elongate flexible shaft having proximal and distal ends,
   lumen means extending through the shaft for communicating fluid and receiving a guidewire;
   a balloon mounted to the distal end of the shaft, and wherein the interior of the balloon is in communication with said lumen means;
   at least a portion of said lumen means being adapted to receive fluid for inflating and deflating the balloon;
   a guidewire extending through said lumen means, a portion of the guidewire extending distally beyond the distal end of the catheter shaft; and
   means for sealing the inflation fluid within the catheter and including a sealed connection of a portion of the shaft in the distal end to the guidewire, and means for selectively rupturing said sealed connection so as to detach the guidewire and said catheter to replace said catheter.

2. A catheter as defined in claim 1 further comprising:
an actuating wire extending along the length of the catheter shaft, the actuating wire having proximal and distal ends, the distal end being integrated into the sealed connection;
the proximal end of the actuating wire being exposed at the proximal end of the catheter and being actuable to rupture the sealed connection.

3. A catheter as defined in claim 2 wherein said actuating wire comprises a pull wire.

4. A catheter as defined in claim 2 wherein the distal end of the actuating wire is coiled about the shaft of the guidewire within the sealed connection.

5. A catheter as defined in claim 4 wherein the sealed connection includes an adhesive bond.

6. A catheter as defined in claim 5 wherein the adhesive bond is adapted to be deteriorated by heat, the actuating wire comprising means for transmitting energy along the catheter shaft to develop heat in the adhesive bond.

7. A catheter as defined in claim 6 wherein the coil at the distal end of the actuating wire comprises a resistance heater and wherein the actuating wire comprises electrically conductive wire means for operating the resistance heater.

8. A catheter as defined in any one of claims 1-3 further comprising:
the proximal end of the guidewire being exposed at the proximal end of the catheter, the proximal end of the guidewire having connector means for connection to an extension wire for extending the effective length of the guidewire.

9. A catheter as defined in claim 4 further comprising:
the proximal end of the guidewire being exposed at the proximal end of the catheter, the proximal end of the guidewire having connector means for connection to an extension wire for extending the effective length of the guidewire.

10. A catheter as defined in claim 5 further comprising:
the proximal end of the guidewire being exposed at the proximal end of the catheter, the proximal end of the guidewire having connector means for connection to an extension wire for extending the effective length of the guidewire.

11. A catheter as defined in claim 6 further comprising:
the proximal end of the guidewire being exposed at the proximal end of the catheter, the proximal end of the guidewire having connector means for connection to an extension wire for extending the effective length of the guidewire.

12. A balloon angioplasty catheter comprising:
an elongate flexible, tubular shaft having proximal and digital ends, and having a lumen extending through the shaft for communicating fluid and receiving a guidewire;
a balloon mounted to the distal end of the shaft, and wherein the interior of the balloon is in communication with said lumen;
at least a portion of said lumen being adapted to receive fluid for inflating and deflating the balloon;
a guidewire extending through said lumen, a portion of said guidewire extending distally beyond the distal end of the catheter shaft;
a sleeve extending about the guidewire along at least the portion of the guidewire extending within the balloon, the sleeve being connected at its distal end to the distal end of the balloon; and
means for sealing the portion of the lumen by which the balloon may be inflated and deflated, and including a sealed connection of the proximal end of the sleeve to the guidewire in the distal region to the guidewire, and means for selectively rupturing said sealed connection so as to detach the guidewire and said catheter to replace said catheter.

13. A catheter as defined in claim 12 further comprising:
an actuating wire extending along the length of the catheter shaft, the actuating wire having proximal and distal ends, the distal end being integrated into the sealed connection;
the proximal end of the actuating wire being exposed at the proximal end of the catheter and being actuable to rupture the sealed connection.

14. A catheter as defined in claim 13 wherein said actuating wire comprises a pull wire.

15. A catheter as defined in claim 13 wherein the distal end of the actuating wire is coiled about the shaft of the guidewire within the sealed connection.

16. A catheter as defined in claim 15 wherein the sealed connection includes an adhesive bond.

17. A catheter as defined in claim 16 wherein the adhesive bond is adapted to be deteriorated by heat, the actuating wire comprising means for transmitting energy along the catheter shaft to develop heat in the adhesive bond.

18. A catheter as defined in claim 17 wherein the coil at the distal end of the actuating wire comprises a resistance heater and wherein the actuating wire comprises electrically conductive wire means for operating the resistance heater.

19. A catheter as defined in claim 12 further comprising:
the proximal end of the guidewire being exposed at the proximal end of the catheter, the proximal end of the guidewire having connector means for connection to an extension wire for extending the effective length of the guidewire.

20. A method for performing an angioplasty procedure comprising:
providing an angioplasty catheter having a shaft, a dilatation balloon carried at the distal end of the shaft and an integral guidewire, the catheter further having means for detaching the catheter shaft and balloon from the guidewire;
inserting the catheter into a patient;
detaching the catheter shaft and balloon from the guidewire; and
withdrawing the detached catheter shaft and balloon from the patient while retaining the guidewire in position within the patient.

21. A method as defined in claim 20 further comprising:
thereafter advancing a second over-the-wire catheter along the guidewire whereby the guidewire may direct the second catheter to the site of the previous catheter.

22. A method as defined in claim 20 further comprising:
before withdrawing the first catheter, attaching an extension wire to the proximal end of the guidewire whereby the exposed portion of the guidewire and extension wire may define a combined length that is greater than the length of either of the catheters.

23. A method as defined in claim 20 further comprising:
thereafter advancing a second over-the-wire catheter of monorail configuration along the guidewire whereby the guidewire may direct the monorail catheter to the site of the previous catheter.

24. A method for performing an angioplasty procedure comprising:
providing an angioplasty over-the-wire catheter having a shaft, a dilatation balloon carried at the distal end of the shaft and an integral guidewire, the shaft and guidewire being sealed to each other in a region proximate to the balloon, the catheter further having means for detaching the catheter shaft and balloon from the guidewire;
inserting the catheter into a patient;
detaching the catheter shaft and balloon from the guidewire;
withdrawing the detached catheter shaft and balloon from the patient while retaining the guidewire in position within the patient; and
thereafter advancing a second over-the-wire catheter along the guidewire whereby the guidewire may direct the second catheter to the site of the previous catheter.

* * * * *